United States Patent
Foguet et al.

(10) Patent No.: US 7,323,433 B2
(45) Date of Patent: Jan. 29, 2008

(54) R-(-)-1-[2-(7-CHLOROBENZO[B]THIOPEN-3-YL-METHOXY)-2-(2,4-DICHLOROPHENYL)-ETHYL]-1H-IMIDAZOLE

(75) Inventors: Rafael Foguet, Barcelona (ES); Jorge Ramentol, Barcelona (ES); Lluis Anglada, Barcelona (ES); Celia Palacin, Barcelona (ES); Antonio Guglietta, Sant Joan Despí (ES)

(73) Assignee: Ferrer Internacional, S.A., Barcelona (ES)

( * ) Notice: Subject to any disclaimer, the term of this patent is extended or adjusted under 35 U.S.C. 154(b) by 328 days.

(21) Appl. No.: 10/911,572

(22) Filed: Aug. 5, 2004

(65) Prior Publication Data

US 2005/0065201 A1    Mar. 24, 2005

Related U.S. Application Data

(63) Continuation-in-part of application No. PCT/EP03/01089, filed on Feb. 4, 2003.

(30) Foreign Application Priority Data

Feb. 11, 2002    (ES) .................... 200200328

(51) Int. Cl.
*A01N 43/50* (2006.01)
*A61K 31/4164* (2006.01)
*C07D 233/54* (2006.01)

(52) U.S. Cl. ............... 504/275; 548/300.1; 548/311.1; 548/311.4; 504/261; 514/385; 514/396; 514/397

(58) Field of Classification Search ............ 548/300.1, 548/311.1, 311.4; 514/385, 396, 397; 504/261, 504/275

See application file for complete search history.

(56) References Cited

U.S. PATENT DOCUMENTS 5,374,633 A * 12/1994 Parab .................. 514/171
5,939,555 A * 8/1999 Foguet et al. ............ 548/311.1

FOREIGN PATENT DOCUMENTS

EP    0 151 477 B1    9/1990
EP    0 748 806 B1    7/1998

OTHER PUBLICATIONS

Manuel Raga et al., Eur. J. Med. Chem.-Chim Ther., 21(4) :329-332 (1986).

* cited by examiner

*Primary Examiner*—Golam M. M. Shameem
(74) *Attorney, Agent, or Firm*—Birch, Stewart, Kolasch & Birch, LLP

(57) ABSTRACT

The invention relates to R-(−)-1-[2-(7-Chloro-benzo[b]thiophen-3-yl-methoxy)-2-(2,4-dichloro-phenyl)-ethyl]-1H-imidazole and the salts thereof. The invention also relates to compositions thereof and their use either for treating fungal infections in humans and animals or combating crop diseases. A process for their preparation is also described.

10 Claims, No Drawings

R-(-)-1-[2-(7-CHLOROBENZO[B]THIOPEN-3-YL-METHOXY)-2-(2,4-DICHLOROPHENYL)-ETHYL]-1H-IMIDAZOLE

This application is a Continuation-In-Part of copending PCT International Application No. PCT/EP03/01089 filed on Feb. 4, 2003, which designated the United States and on which priority is claimed under 35 U.S.C. § 120, which claims priority under 35 U.S.C. § 119(a) on Patent Application No(s). 200200328 filed in Spain on Feb. 11, 2002, the entire contents of which are hereby incorporated by reference.

DESCRIPTION

The present invention relates to R-(−)-1-[2-(7-chlorobenzo [b]thiophen-3-yl-methoxy)-2-(2,4-dichlorophenyl) -ethyl]-1-imidazole (R-(−)-sertaconazole) and its salts, a process for its preparation, compositions which comprise said compound and the use of same for treating fungal infections and combating crop diseases.

Racemic 1-[2-(7-chlorobenzo[b]thiophen-3-yl-methoxy)-2-(2,4-dichlorophenyl)-ethyl ]-1H-imidazole—is a useful antifungal agent as sertaconazole (WHO, INN)—is a useful antifungal agent for treatment of diseases caused by fungi and yeasts in man and in animals. Its preparation and that of its mononitrate are disclosed in European Patent No. 151.477.

The present invention relates to R-(−)-1-[2-(7-chlorobenzo [b]thiophen-3-yl-methoxy)-2-(2,4-dichlorophenyl) -1H-imidazole of formula (I):

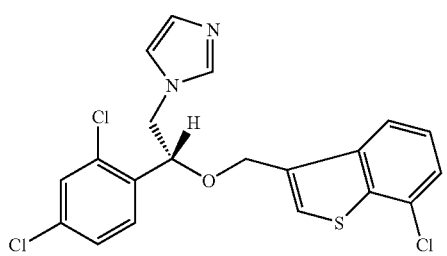

as well as its pharmaceutically acceptable addition salts.

The R-(−)-enantiomer of sertaconazole possesses an activity of about 2 times higher than that of the racemic mixture, against both fungi and yeasts (because its affinity to the target is 2 times higher) as shown in Table 1. This finding has enabled to formulate R-(−)-sertaconazole at doses ½ of those used for racemic sertaconazole, thus providing a reduced risk of side effects and the suppression of unspecific toxicity due to the unwanted fraction of the S-(+)-enantiomer.

The mononitrate is the preferred salt of R-(−)-sertaconazole.

The present invention also relates to a process for the preparation of the R-(−)-enantiomer of sertaconazole and its pharmaceutically acceptable addition salts which process comprises reacting R-(−)-1-(2,4-dichlorophenyl)-2-imidazol-1-yl-ethanol of formula ((R)-(−)-III):

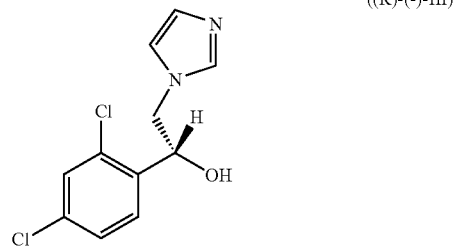

with 3-halomethyl-7-chlorobenzo[b]thiophene of formula (IV):

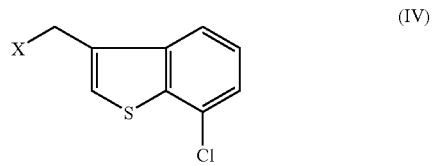

wherein X is halogen.

The compound can be recovered from the reaction mixture in a manner known per se. If desired, the crude product can be further purified by methods well known in the art, e.g. crystallisation and/or chromatography.

The preparation of the S-(+)-enantiomer of sertaconazole can be accomplished accordingly using S-(+)-1-(2,4-dichlorophenyl)-2-imidazol-1-yl-ethanol instead of the R-(−)-enantiomer.

A prerequisite for the preparation of the enantiomers of sertaconazole according to the above process is to prepare the appropriate enantiomers of intermediate 1-(2,4-dichlorophenyl)-2-imidazol-1-yl-ethanol (III).

The two enantiomers of 1-(2,4-dichlorophenyl)-2-imidazol-1-yl-ethanol (III) can be prepared by resolution of the corresponding racemic mixture with an optically active acid, preferably L-tartaric acid, D-tartaric acid, dibenzoyl-L-tartaric, dibenzoyl-D-tartaric acid or the like, according to the method described in GB Patent No. 1.244.530 and in Lammerhofer M. and Lindner W. (Chirality 6:261-269, 1994). (R)-(−)-1-(2,4-dichloro-phenyl)-2-imidazol-1-yl-ethanol is also prepared by the enantioselective reduction of 1-(2,4-dichlorophenyl)-2-imidazol-1-yl-ethanone (II) using (−)-β-chlorodiisopino-camphenylborane, [(−)-DIP chloride] leading to (R)-(−)-1-(2,4-dichlorophenyl)-2-imidazol-1-yl-ethanol ((R-(−)-III) with an acceptable optical purity.

The reaction of one of the enantiomers of the intermediate of formula (III) with 3-halomethyl-7-chlorobenzo[b] thiophene (IV) is carried out to yield the corresponding enantiomer of sertaconazole as free base. Among 3-halomethyl-7-chlorobenzo[b]thiophenes, 3-chloromethyl-7-chlorobenzo[b]thiophene and 3-bromomethyl-7-chloro-benzo[b] tiophene are preferred.

The enantiomers of sertaconazole as free bases can be converted into the pharmaceutically acceptable salts in a manner known per se. Preferably, the mononitrates are obtained by treating with nitric acid.

The reaction steps for the preparation of the enantiomers of sertaconazole are shown in the following scheme.

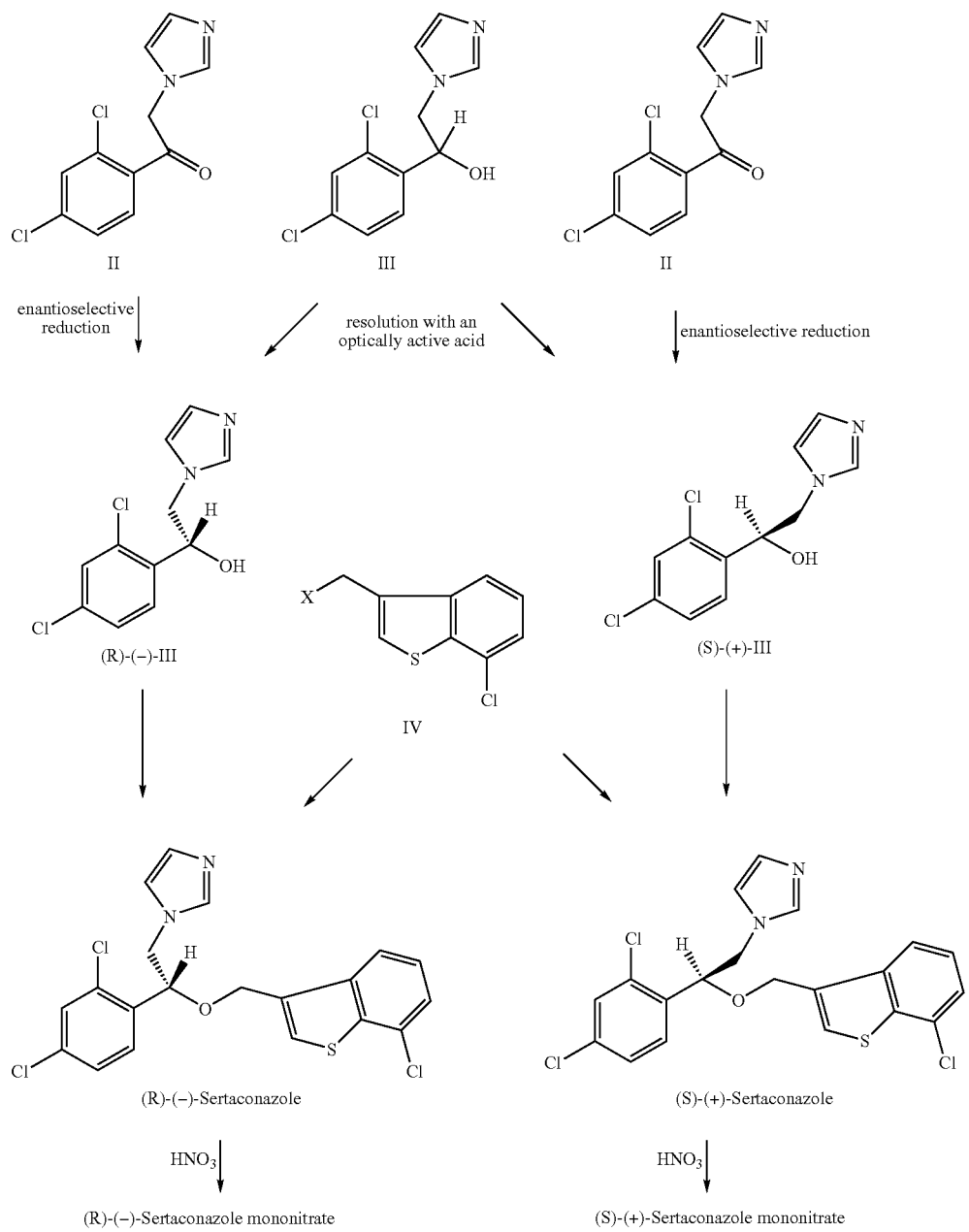

The present invention further relates to pharmaceutical compositions comprising R-(−)-sertaconazole and/or a salt thereof and to the use of R-(−)-sertaconazole and/or a salt thereof for the treatment of infections caused by fungi and yeasts in both the man and pets, as well as against crop diseases caused by such microorganisms.

The compounds of the present invention, optionally mixed with pharmacologically acceptable carriers, can be administered to humans or animals by the oral route in the form of tablets, capsules, coated tablets, syrups, solutions, powders, granules, emulsions, oral gels, oral pastes, buccopharyngeal solutions, buccopharyngeal suspensions, buccopharyngeal gels, buccopharyngeal pastes, etc., by injectable route, by rectal route and by vaginal-intrauterine route in the form of ovulum, vaginal tablet, vaginal capsule, medicated vaginal tampon, ointment, cream, gel, foam, solution, emulsion, suspension, pessary, lotion, etc., at daily doses ranging from 50 to 400 mg; and by topical route in the form of cream, lotion, paste, suspension, ointment, emulsion, solution, foam, shampoo, powder, gel, etc., at concentrations ranging from 0.05 to 3%.

Also the compounds of the present invention, optionally in admixture with a diluent or carrier when used against crop diseases can be applied by watering, atomising, spraying, dusting, or in the form of powder, cream, paste, etc., at the rate of 0.05-10 Kg per hectare of soil.

The following Examples will illustrate the preparation of the enantiomers of sertaconazole, pharmaceutical formulations containing them and their biological activity on various microorganisms.

EXAMPLE 1

R-(−)-1-(2,4-dichlorophenyl)-2-imidazol-1-yl-ethanol

In a 50-ml one-necked flask equipped with an addition funnel, cooling bath, magnetic stirrer and nitrogen gassing device 3.14 g (9.8 mmol, 2.5 eq.) of (−)-DIP chloride and 9 ml of anhydrous ethyl ether (molecular screens 4 Å) are mixed. To the resultant mixture, a solution of 1 g (3.92 mmol, 1 eq.) of 1-(2,4-dichlorophenyl)-2-imidazol-1-yl-ethanone in 10 ml of anhydrous tetrahydrofuran (molecular screens 4 Å) is added drop by drop at room temperature under nitrogen atmosphere. The mixture is stirred for 24 hours at room temperature under nitrogen atmosphere. 0.4 ml of methanol are added, stirred for 10 min, and the solvents are removed by reduced-pressure evaporation.

To the resultant crude, 10 ml of n-hexane and 10 ml of water are added. The mixture is acidified by adding 1.6 ml of 6 M hydrochloric acid. The two phases are separated and the organic layer is removed. The aqueous phase is neutralised with 3M NaOH until pH=10-11 in the presence of 10 ml of ethyl ether. The two phases are separated, and the organic layer is washed with 10 ml of ethyl ether. The two ethereal layers are dried over anhydrous sodium sulphate and evaporated to dryness by reduced-pressure distillation. 1.27 g of crude product are yielded and crystallised from a mixture of 5 ml of ethanol-water 1:1 v/v to give 0.8 g (R=80%) of (R)-(−)-1-(2,4-dichloro-phenyl)-2-imidazol-1-yl-ethanol.

Analytical data: DSC: peak at 107.4° C. IR spectrum: conforms $^1$H-$^{13}$C-NMR (DMSO) spectrum: conforms $[\alpha]^{D20}$ (c=6%, MeOH)=−80

EXAMPLE 1'

R-(−)-1-(2,4-dichloro-phenyl)-2-imidazol-1-yl-ethanol

A solution of 5 g of 1-(2,4-dichloro-phenyl)-2-imidazol-1-yl-ethanol in a mixture of acetone-methanol (25 ml-20 ml) was added slowly to D-tartaric acid (3.21 g) dissolved in a mixture of acetone-methanol (25 ml-10 ml), at room temperature. When the addition was completed, the reaction mixture was stirred for 30 additional minutes at room temperature. The solid obtained was filtered and recrystallized in methanol. Isolated yield: 1.85 g (37%), enantiomeric purity: >98% R-isomer.

EXAMPLE 2

(R)-(−)-1-[2-(7-Chlorobenzo[b]Thiophen-3-yl-Methoxy)-2-(2,4-dichlorophenyl)-Ethyl]-1H-imidazole In a 100-ml three-necked flask equipped with a reflux cooler, immersion thermometer, addition funnel, cooling bath, and nitrogen gassing device 10 ml of dry N,N-dimethylformamide (molecular screens 4 Å) and 1.27 g (11.3 mmol, 1.03 eq.) of potassium t-butoxide are mixed. To the resultant mixture, cooled in a water bath, a solution of 2.83 g (11 mmol) of (R)-(−)-1-(2,4-dichlorophenyl)-2-imidazol-1-yl-ethanol in 15 ml of dry N,N-dimethylformamide are added drop by drop. After the addition is completed, the mixture is stirred for 45 minutes and added to a solution of 2.93 g (11.2 mmol, 1.02 eq.) of 3-bromomethyl-7-chlorobenzo[b]thiophene in 7 ml of dry N,N-dimethyl-formamide. The reaction mixture is stirred for 4 hours at room temperature. The solvent is evaporated by reduced-pressure distillation and the residue is treated with 50 ml of methylene chloride. The resultant solution is washed twice with 30 ml of water, dried over anhydrous sodium sulphate, filtered and evaporated to dryness by reduced-pressure distillation to yield 4.62 g of crude product. The crude product obtained is purified by silicagel column chromatography using a gradient of methylene chloride-methanol as an eluant. A resin (2.0 g) is obtained which is crystallised from ethyl ether (10 ml). The solid formed is filtered and dried to give 1.22 g (R=25.1%) of (R)-(−)-1-[2-(7-chlorobenzo[b]thiophen-3-yl-methoxy)-2-(2,4-dichlorophenyl)-ethyl]-1H-imidazole.

Analytical data: DSC: peak at 74.5° C. IR spectrum: conforms $^1$H-$^{13}$C-NMR (DMSO) spectrum: conforms $[\alpha]^{D20}$ (c=1%, MeOH)=−61.0

EXAMPLE 3

(S)-(+)-1-[2-(7-chlorobenzo[b]thiophen-3-yl-methoxy)-2-(2,4-dichlorophenyl)-ethyl]-1H-imidazole In a 100-ml three-necked flask equipped with a reflux cooler, immersion thermometer, addition funnel, cooling bath, and nitrogen gassing device 16 ml of dry N,N-dimethylformamide (molecular screens 4 Å) and 2.04 g (18.43 mmol, 1.05 eq.) of potassium t-butoxide are mixed. To the resultant mixture, cooled in a water bath, a solution of 4.44 g (17.2 mmol) of (S)-(+)-1-(2,4-dichlorophenyl)-2-imidazol-1-yl-ethanol in 25 ml of dry N,N-dimethylformamide are added drop by drop. After the addition is completed, the mixture is stirred for 45 minutes and added to a solution of 4.61 g (17.62 mmol, 1.02 eq.) of 3-bromomethyl-7-chlorobenzo[b]thiophene in 13 ml of dry N,N-dimethyl-formamide. The reaction mixture is stirred for 4 hours at room temperature. The solvent is evaporated by reduced-pressure distillation and the residue is treated with 80 ml of methylene chloride. The resultant solution is washed twice with 50 ml of water, dried over anhydrous sodium sulphate, filtered and evaporated to dryness by reduced-pressure distillation to yield 7.30 g of crude product. The crude product obtained is purified by silicagel column chromatography using a gradient of methylene chloride-methanol as an eluant. A resin (3.78 g) is obtained which is crystallised from ethyl ether (18 ml). The solid formed is filtered and dried to give 2.61 g (R=34.5%) of (S)-(+)-1-[2-(7-chlorobenzo[b]thiophen-3-yl-methoxy)-2-(2,4-dichlorophenyl)-ethyl]-1H-imidazole.

Analytical data: DSC: peak at 83.4° C. IR spectrum: conforms $^1$H-$^{13}$C-NMR (DMSO) spectrum: conforms $[\alpha]^{D20}$ (c=1%, MeOH)=+69

EXAMPLE 4

(R)-(−)-Sertaconazole Mononitrate ((R)-(−)-1-[2-(7-Chlorobenzo[b]Thiophen-3-yl-Methoxy)-2-(2,4-dichloro-Phenyl)-Ethyl]-1H-Imidazole Monoitrate)

880 mg (2.01 mmol) of (R)-(−)-1-[2-(7-chlorobenzo[b]thiophen-3-yl-methoxy)-2-(2,4-dichlorophenyl)-ethyl]-1H-imidazole are dissolved in 5 ml of 96% ethanol. 1 ml of water is added and heated at a temperature between 35 and 37° C. To the obtained solution, 0.23 ml of 60% nitric acid (3 mmol, 1.5 eq.) are added. Then 3 ml of water are added and cooled first at room temperature and thereafter at 10° C. for 1 hour. The formed solid is filtered, washed twice with 4 ml of water and dried at vacuum for 24 hours to give 0.9 g (R=89%) of (R)-(−)-1-[2-(7-chlorobenzo[b]thiophen-3-yl-methoxy)-2-(2,4-dichlorophenyl)-ethyl]-1H-imidazole mononitrate.

Analytical data: DSC: peak at 116.87° C. IR spectrum: conforms $^1$H-$^{13}$C-NMR (DMSO) spectrum: conforms $[\alpha]_D^{20}$ (c=1%, MeOH)=−85.00

EXAMPLE 4'

(R)-(−)-sertaconazole mononitrate ((R-(−)-1-[2-(7-chloro-benzo[b]thiophen-3-yl-methoxy)-2-(2,4-dichlorophenyl)-ethyl]-1H-imidazole mononitrate)

In a 500 ml flask, equipped with mechanical stirrer was charged 15.72 9 of R-(−)-1-(2,4-dichloro-phenyl)-2-imidazol-1-yl-ethanol, 45 ml of toluene, 1.05 g of tetrabutylammonium hydrogen sulphate and 24.5 g of 18 N aqueous NaOH. The mixture was heated to 35-40° C. and the temperature kept for 15 additional minutes. Then, a solution of 3-bromomethyl-7-cloro-benzo[b]thiophene in 376 ml of toluene was added in 30 minutes. The temperature was kept 2.5 hours between 37 and 40° C., and then water was added. The orgainic layer was washed with water. After concentrating at reduced pressure, the crude product was dissolved in 150 ml of absolute ethanol. A mixture of 9.1 g of 60% HNO$_3$ and 130 ml of water was slowly added and when the addition was completed, the reaction mixture was cooled to 0° C. The solid obtained was filtered, recrystallized in acetone-ethanol and dried. Isolated yield: 24.5 g (80%).

EXAMPLE 5

(S)-(+)-sertaconazole mononitrate ((S)-(+)-1-[2-(7-chlorobenzo[b]thiophen-3-yl-methoxy)-2-(2,4-dichloro-phenyl)-ethyl]-1H-imidazole monoitrate)

2.35 mg (5.37 mmol) of (S)-(+)-1-[2-(7-chlorobenzo[b]thiophen-3-yl-methoxy)-2-(2,4-dichlorophenyl )-ethyl]-2H-imidazole are dissolved in 17 ml of 96% ethanol. 3 ml of water are added and heated at a temperature between 35 and 40° C. To the obtained solution, 0.61 ml of 60% nitric acid (8.06 mmol, 1.5 eq.) are added. Then 13 ml of water are added and cooled first at room temperature and thereafter at 10° C. for 1 hour. The formed solid is filtered, washed twice with 10 ml of water and dried at vacuum for 24 hours to give 2.65 g (R=98.5%) of (S)-(+)-1-[2-(7-chloro-benzo[b]thiophen-3-yl-methoxy)-2-(2,4-dichlorophenyl)-ethyl]imidazole mononitrate.

Analytical data: DSC: peak at 168.91° C. IR spectrum: conforms $^1$H-$^{13}$C-NMR (DMSO) spectrum: conforms $\alpha]_D^{20}$ (c=1%, MeOH)=+89.00

EXAMPLE 6

1% Cream Formulation

| Composition for 100 g | |
|---|---|
| R-(−)-Sertaconazole mononitrate | 1.00 g |
| Palmitic and stearic acid mono- and diglyceride | 6.00 g |
| Ketostearyl alcohol with 20 mol of ethylene oxide | 1.00 g |
| Oleic acid decyl ester | 5.00 g |
| Undecylenic acid monoethanolamine | 2.00 g |
| Carbomer | 1.00 g |
| Triethanolamine | 0.60 g |
| Methylparaben | 0.15 g |
| Propylparaben | 0.05 g |
| Distilled water to volume | 100.00 g |

EXAMPLE 7

1% Gel Formulation

| Composition for 100 g | |
|---|---|
| R-(−)-Sertaconazole mononitrate | 1.00 g |
| Propylene glycol | 10.00 g |
| Carbomer | 1.00 g |
| Tween 20 | 0.10 g |
| Phenoxyethanol | 0.35 g |
| EDTA disodium | 0.15 g |
| Citric acid | 0.25 g |
| 1 N Sodium hydroxide | 1.50 g |
| Triethanolamine | 1.55 g |
| Distilled water to volume | 100.00 g |

EXAMPLE 8

Biological Data

Minimal Inhibitory Concentrations (MICs) were determined by using a modification of the microdilution method M27-A recommended by the National Committee for Clinical Laboratory Standards in RPMI-1640 medium (Sigma) supplemented with glucose to a concentration of 2% and adjusted to pH 7.0 with 0.165 M morpholine propanesulfonic (MOPS) acid buffer. Serial twofold dilutions were made in modified RPMI-1640 medium from stock solutions. MICs were defined as the lowest drug concentrations resulting in 50% inhibition of growth compared to that of the growth control. The microbiological activities, expressed as geometric means, of R-(−)sertaconazole in comparison with the S-(+)-enantiomer, which is much less active, and with racemic sertaconazole are shown in Table 1. The number of strains used in the experiments is given in parenthesis below the name of each microorganism.

TABLE 1

| MIC (μg/ml) of Sertaconazole nitrate and its enantiomers | | | |
|---|---|---|---|
| Microorganism | R-(−)enantiomer | Racemate | S-(+)enantiomer |
| *Candida* spp (42) | 0.125 | 0.256 | 3.217 |
| *Dermatophytes* (17) | 0.04 | 0.08 | 0.17 |
| *Filamentous fungi* (11) | 1.76 | 3.11 | 16 |
| *Malassezia* spp (11) | 0.64 | 1.37 | 10.96 |

The invention claimed is:
1. R-(−)-1-[2-(7-chlorobenzo[b]thiophen-3-yl-methoxy)-2-(2,4-dichlorophenyl)-ethyl]-1H-imidazole of formula (I):

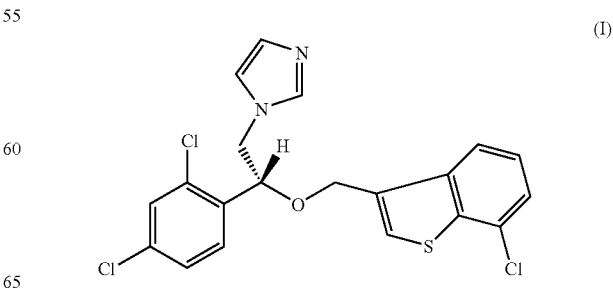

and pharmaceutically acceptable salts thereof.

2. R-(−)-1-[2-(7-chlorobenzo[b]thiophen-3-yl-methoxy)-2-(2,4-dichlorophenyl)-ethyl]-1H-imidazole mononitrate.

3. A process for preparing a compound according to claim 1 or claim 2, comprising reacting R-(−)-1-(2,4-dichlorophenyl)-2-imidazol-1-yl-ethanol of formula ((R)-(−)-III):

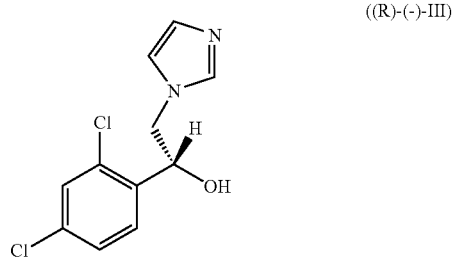

((R)-(−)-III)

with 3-halomethyl-7-chlorobenzo[b]thiophene of formula (IV):

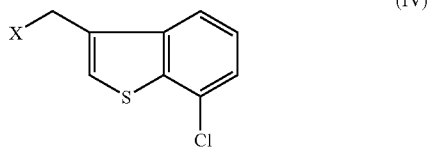

(IV)

wherein X is halogen, and optionally treating the resulting R-(−)-1-[2-(7-chlorobenzo[b]thiophen-3-yl-methoxy)-2-(2, 4-dichlorophenyl)-ethyl]-1H-imidazole with a salt-forming acid.

4. The process according to claim 3, wherein X is chlorine or bromine.

5. The process according to claim 3, wherein the compound is R-(−)-1-[2-(7-chlorobenzo[b]thiophen-3-yl-methoxy)-2-(2,4-dichlorophenyl)-ethyl]-1H-imidazole mononitrate and the salt-forming acid is nitric acid.

6. The process according to claim 3, wherein R-(−)-1-2,4-dichlorophenyl)-2-imidazol-1-yl-ethanol of formula ((R)-(−)-(III) is prepared by enantioselective reduction of 1-(2,4-dicblorophenyl)-2-imidazol-1-yl-ethanone with (−)-βchlorodiisopino-camphenylborane.

7. The pharmaceutical composition comprising:
   R-(−)-1-[2-(7-chlorobenzo[b]thiophen-3-yl-methoxy)-2-(2,4-dichlorophenyl)-ethyl]-1H-imidazole or a salt thereof; and
   a pharmacologically acceptable carrier.

8. An agricultural composition comprising:
   R-(−)-1-[2-(7-chlorobenzo[b]thiophen-3-yl-methoxy)-2-(2,4-dichlorophenyl)-ethyl]-1H-imidazole mononiftate; and
   a diluent or carrier.

9. The method of treating fungal infections in a human or animal, said method comprising administering an effective amount of R-(−)-1-[2-(7-chlorobenzo [b]thiophen-3-yl-methoxy)-2-(2,4-dichlorophenyl)-ethyl]-1H-imidazole or a salt thereof to said human or animal.

10. The method of treating a crop disease, said method comprising administering an effective amount of R-(−)-1-[2-(7-chlorobenzo[b]thiophen-3-yl-methoxy)-2-(2,4-dichlorophenyl)-ethyl]-1H-imidazole mononitrate or the salt thereof to the crop.

* * * * *

UNITED STATES PATENT AND TRADEMARK OFFICE
CERTIFICATE OF CORRECTION

PATENT NO. : 7,323,433 B2
APPLICATION NO. : 10/911572
DATED : January 29, 2008
INVENTOR(S) : Rafael Fouget et al.

It is certified that error appears in the above-identified patent and that said Letters Patent is hereby corrected as shown below:

Title page:
Item (75), INVENTORS, should read as: "Rafael Fouget, Barcelona (ES); Jorge Ramentol, Barcelona (ES);" Lluis Anglada, Barcelona (ES); Celia Palacin, Barcelona (ES); Antonio Guglietta, Barcelona (ES)

Column 7, lines 1-3:
Lines 1-3 should read as follows: Analytical data: DSC: peak at "116.87°C," --168.7°C,-- IR spectrum: conforms $^1$H-$^{13}$C-NMR (DMSO) spectrum: conforms $[\alpha]_D^{20}$ (c = 1%, MeOH) = -85.00

Signed and Sealed this

First Day of June, 2010

David J. Kappos
*Director of the United States Patent and Trademark Office*